United States Patent [19]
Lin et al.

[11] Patent Number: 5,962,012
[45] Date of Patent: Oct. 5, 1999

[54] CHOLINERGIC ANTAGONIST PATCH

[75] Inventors: Wan-Yan Lin; Shu-Juan Chen; Chao-Wei Liao, all of Hsinchu; Chien-Hsin D. Cheng, Hsinchu Hsien, all of Taiwan

[73] Assignee: Caleb Pharmaceuticals, Inc., Hsinchu, Taiwan

[21] Appl. No.: 09/022,308

[22] Filed: Feb. 11, 1998

[30] Foreign Application Priority Data

Nov. 28, 1997 [TW] Taiwan ................................ 86117918

[51] Int. Cl.$^6$ ...................................... A61F 13/02
[52] U.S. Cl. ........................ 424/448; 514/292; 514/946; 514/947
[58] Field of Search ............................ 424/448; 514/946, 514/947, 292

[56] References Cited

U.S. PATENT DOCUMENTS 5,006,342  4/1991  Cleary et al. ........................ 424/445
5,811,117  9/1998  Hashimoto et al. .................. 424/448
5,834,010  11/1998 Quan et al. .......................... 424/448

*Primary Examiner*—Thurman K. Page
*Assistant Examiner*—Alysia Berman
*Attorney, Agent, or Firm*—Merchant, Gould, Edell, Welter & Schmidt, P.A.

[57] ABSTRACT

Scopolamine is a folksy cholinergic antagonist, and is used by parasympathetic nerves in autonomic nervous neurons as an anti-motion sickness drug or an anti-emesis drug. Since the human body most effectively absorbs this drug through the postauricular skin, the drug is administered by postauricular transdermal resorption patch. The penetrability of drug is increase by adding a dermal penetrative enhancer, because the penetration ability of patch-administered drugs is usually decreased by the penetrative blockade at dermal horny layers. The present invention discloses a penetration enhancer to increase dermal absorption and penetration of the cholinergic antagonist. The present invention finds that polyethylene and amide enhance penetration, about 2.2–2.8 fold. In accordance with the present invention, a penetration enhancer is added to the formulations of transdermal patch to increase the human body's absorption of scopolamine.

7 Claims, 2 Drawing Sheets

CHOLINERGIC ANTAGONIST PATCH

CROSS-REFERENCE TO RELATED APPLICATION

This application claims the priority benefit of Taiwan application serial no. 86117918, filed Nov. 28, 1997, the full disclosure of which is incorporated herein by reference.

BACKGROUND OF THE INVENTION

1. Field of the Invention

The invention relates in general to a new cholinergic antagonist patch, and more particularly to a new dermal penetration enhancer for cholinergic antagonist patch.

2. Description of the Related Art

Scopolamine is one of several folksy cholinergic antagonists which selectively block the muscarinic receptors of the parasympathetic nerves in the autonomic nervous system. These medicines inhibit all actions of the parasympathetic nerves, and block some of the cholinergic sympathetic neurons, like the sweat gland nerves. However, they have no effect on other autonomic nervous neurons. The cholinergic antagonist is empirically applied as an anti-motion sickness drug, cycoplegics drug and is used with anesthetics in birth. They are also used to remedy some neurologic diseases.

Scopolamine is administered by a patch affixed to the postauricular skin for transdermal absorption. It is absorbed by the skin and transmitted to targets. Since the dermal horny layer is an ordered array of steato-dissoluble protecting films, it stops both dispersion of mist and penetration of foreign materials. General drugs have difficulty entering the body fluid through the horny layer barrier. Resistance to drug penetration varies with racial skin type. A dermal penetration enhancer circumvents the racial differences and serves to carry the medicine into the body's fluids.

The penetration enhancer may be a surfactant of some sort. This compound is usually used as a component of various paints to help the carry of the main component, or as a emulsion for the cosmetic maintenance of skin. The surfactant usually has one lipophilic long carbonous chain terminal group and one hydrophilic hydroxyl or amine terminal group. These terminal groups bond with the main component as a carrier. The composition always plays an important part in the medicine design.

The choice of an appropriate surfactant is important since dermal penetration ability of surfactant varies, depending on the drug bound to it. In order to choose an appropriate penetration enhancer, the present invention uses different surfactants with scopolamine to compare dermal penetration abilities. In addition, this invention compares concentration intergrade in dermal penetration to discover the nature of the penetration ability.

SUMMARY OF THE INVENTION

It is therefore an object of the invention to provide an new formulation for dermal penetration enhancers to increase absorption of cholinergic antagonists from the scopolamine patch.

In accordance with the foregoing and other objectives of the present invention, a new dermal penetration enhancer is provided to enhance the dermal absorption and to saturate of the scopolamine patch in cholinergic antagonists. The components of the patch are a polyacrylic pressure sensitive adhesive (PSA), scopolamine and a penetration enhancer. The penetration enhancer is made from a surfactant derivative of polyethylene glycol and a surfactant derivative of amide. In addition, the present invention finds that the surfactant of polyethylene glycol and the surfactant of amide have an additive penetrative effect. Increase in penetration is about 2.2 to 2.8 fold. Through the present invention, the addition of the penetration enhancer to the formulation ensures transdermal absorption from the scopolamine patch and effective administration of the drug.

BRIEF DESCRIPTION OF THE DRAWINGS

Other objects, features, and advantages of the invention will become apparent from the following detailed description of the preferred but non-limiting embodiments. The description is made with reference to the accompanying drawings in which.

DESCRIPTION OF THE PREFERRED EMBODIMENT

Referring to drawings, a new cholinergic antagonist patch in accordance with the present preferred embodiment of this invention will be described below.

Figure 1:
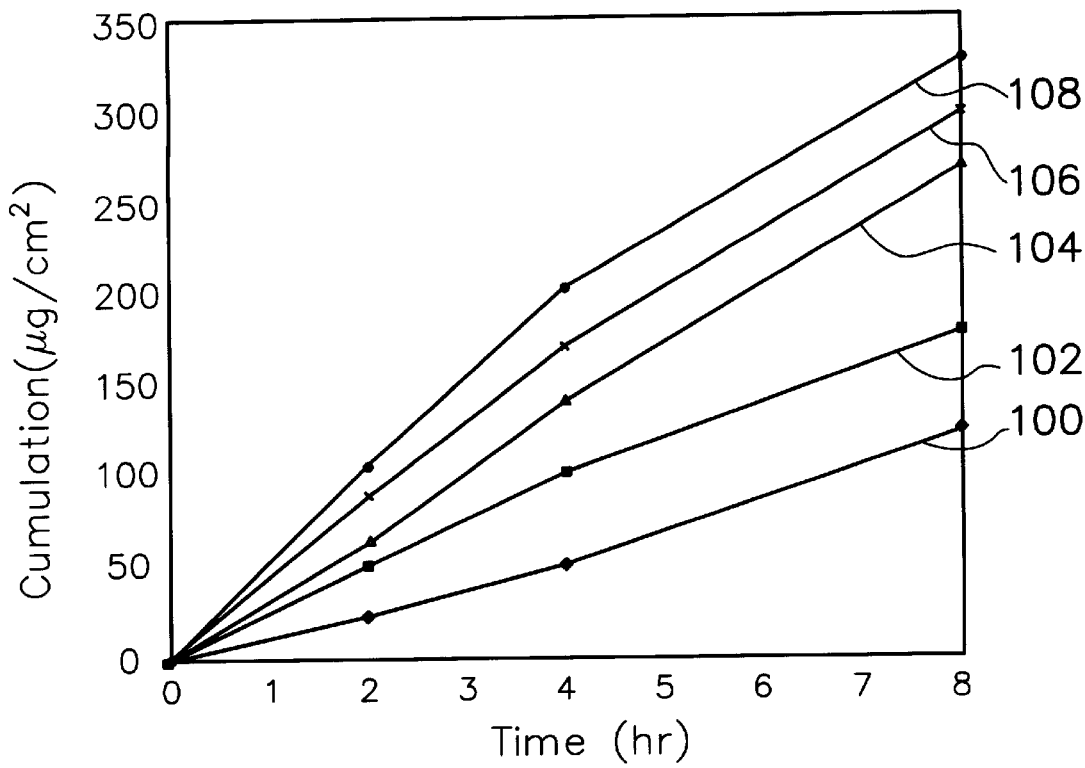
FIG. 1 is a diagram showing the effect of adding the dermal enhancer a compound containing 90% lauric acid diethanolamide and 6% diethanolamine, and polyethylene glycol glyceryl caprylate versus the transdermal scopolamine of the present invention.

Referring first to FIG. 1, for exhibiting the fineness of this present invention, an example of which is illustrated. The formulation of the scopolamine patch is illustrated in accompanying description. Polyacrylic pressure sensitive adhesive 2516 is the base provided, for example, by National Starch. 3.5% scopolamine in polyacrylic pressure sensitive adhesive 2516 is added to make formulation P. Next, an enhancer is added to formulation P. Five different additions are described as follows: (1) no addition; (2) 2.5% of the compound containing 90% lauric acid diethanolamide and 6% diethanolamine is added to formulation P, for example, Alkamide LE, provided by Rhone-Poulenc company; (3) 2.5% of the compound containing 90% lauric acid diethanolamide and 6% diethanolamine, and 1.0% of polyethylene glycol glyceryl caprylate are added to formulation P, for example, Labrasol provided by Gattefosse company; (4) 2.5% of the compound containing 90% lauric acid diethanolamide and 6% diethanolamine, and 2.5% of polyethylene glycol glyceryl caprylate are added to formulation P; (5) 2.5% of the compound containing 90% lauric acid diethanolamide and 6% diethanolamine, and 5.0% of polyethylene glycol glyceryl caprylate are added to formulation P. In summary, five formulations are made with the following compositions: P, P-AL2.5, P-AL2.5-L1.0, PAL2.5-L2.5, and P-AL2.5-L5.0. Extracorporeal dermal penetrative tests were also performed, using a sample of human dermal horny layer which is indexed 2913. A graph of drug accumulation versus time showed the result, as illustrated in the FIG. 1. Formulation P is foliated 100, P-AL2.5 is foliated 102, P-AL2.5-L1.0 is foliated 104, P-AL2.5-L2.5 is foliated 106 and P-AL2.5-L5.0 is foliated 108.

The following table illustrates the enhanced effect shown in FIG. 1. The present invention shows the developmental of enhancers by demonstrating dermal penetrative rate Jss($\mu$g/cm$^2$/hr) over eight hours. It enhances the dermal penetration of scopolamine by using a dermal penetration enhancer comprising the compound containing 90% lauric acid diethanolamide and 6% diethanolamine, or polyethylene glycol glyceryl caprylate. Adding two dermal penetration enhancers at the same time, as illustrated in the forgoing description of formulation P increases the dermal penetrative rate about 2.2–2.8 times. This shows that two dermal penetration enhancers illustrated in the forgoing description further enhance the dermal penetrative rate.

| Substitute | Added enhancer | Jss ($\mu$g/cm$^2$/hr) in 8 hr | Penetrative rate ($\mu$g/cm$^2$/hr) | enhance-ement factor |
|---|---|---|---|---|
| P | — | 115 | 14.1 | 1 |
| P-AL2.5 | 2.5% Alkamide LE | 171 | 21.2 | 1.5 |
| P-AL2.5-L1.0 | 2.5% Alkamide LE 1.0% Labrasol | 257 | 32.1 | 2.3 |
| p-AL2.5-L2.5 | 2.5% Alkamide LE 2.5% Labrasol | 288 | 36.0 | 2.5 |
| P-AL2.5-L5.0 | 2.5% Alkamide LE 5.0% Labrasol | 323 | 40.3 | 2.8 |

According to the present invention, the above-mentioned surfactants have a dermal penetrative enhanced effect and increase the dermal penetration of scopolamine. In those surfactants described above, derivatives of polyethylene surfactants include polyethylene glycol glyceryl caprylate and polyethylene glycol -6 glyceryl mono oleate. The derivatives of amide surfactants include the compound containing 90% lauric acid diethanolamide and 6% diethanolamine, and the compound containing 90% coconut fatty acid diethanolamine and 6% diethanilamine. For example, the derivatives of polyethylene surfactants are provided by Gattefosse company and named Labrafil M1944 CS, and the derivatives of amide surfactants are provided by Rhone-Poulenc company and named Alkamide LE. By the result of the foregoing steps, it can be seen that a consequence of the present invention is that the surfactants amide and polyethylene enhance the dermal penetration of scopolamine. So these surfactants are called dermal penetration enhancers.

A test of the dermal medicine penetration is conducted by choosing various polyacrylic pressure sensitive adhesive and comparing them to the compound containing 90% lauric acid diethanolamide and 6% diethanolamine, and polyethylene glycol glyceryl caprylate. Referring to FIG. 2, three formulations are formed by adding the surfactant penetration enhancer, the compound containing 90% lauric acid diethanolamide and 6% diethanolamine, and polyethylene glycol glyceryl caprylate, to the formulation comprising the polyacrylic pressure sensitive adhesive 2516 and 10% scopolamine. The three formulations are: (1) polyacrylic pressure sensitive adhesive 2516 and 10% scopolamine; (2) polyacrylic pressure sensitive adhesive 2516, 10% scopolamine and 5% polyethylene glycol glyceryl caprylate; and (3) crylic piezo-collide 2516, 10% scopolamine and 5% of the compound containing 90% coconut fatty acid diethanolamide and 6% diethanolamine. The three curves show the results of a dermal penetrative test of the samples on dermal horny layers substitute 2913. These include: (1) polyacrylic pressure sensitive adhesive 2516 and 10% scopolamine 110; (2) polyacrylic pressure sensitive adhesive 2516, 10% scopolamine and 5% polyethylene glycol glyceryl caprylate 112; and (3) crylic piezocollide 2516, 10% scopolamine and 5% of the compound containing 90% coconut fatty acid diethanolamide and 6% diethanolamine 114. In accordance with the result showed in FIG. 2, the ability to enhance the compound containing penetration of 90% coconut fatty acid diethanolamide and 6% diethanolamine is better than which of polyethylene glycol glyceryl caprylate.

Referring to FIG. 3, three formulations are formed by adding the surfactant penetration enhancer, 90% lauric acid diethanolamide 6% diethanolamine and polyethylene glycol glyceryl caprylate to the formulation formed with polyacrylic pressure sensitive adhesive MA31 and 10% scopolamine. MA31, for example, is provided by Adhesive Research company. The three formulations include: (1) polyacrylic pressure sensitive adhesive MA31 and 10% scopolamine; (2) polyacrylic pressure sensitive adhesive MA31, 10% scopolamine and 5% polyethylene glycol glyceryl caprylate; and (3) polyacrylic pressure sensitive adhesive MA31, 10% scopolamine and 5% of the compound containing 90% lauric acid diethanolamide and 6% diethanolamine. Data for the three curves come from a dermal penetrative test of the samples about the dermal horny layers substitute 2913. These include: (1) polyacrylic pressure sensitive adhesive MA31 and 10% scopolamine 116; (2) polyacrylic pressure sensitive adhesive MA31, 10% scopolamine and 5% polyethylene glycol glyceryl caprylate 118; and (3) polyacrylic pressure sensitive adhesive MA31, 10% scopolamine and 5% of the compound containing 90% lauric acid diethanolamide and 6% diethanolaminel20. In accordance with the result showed in FIG. 3, the compound containing 90% coconut fatty acid diethanolamide and 6% diethanolamine enhances the dermal penetrative rate of scopolamine, but the enhanced effect of polyethylene glycol glyceryl caprylate is fractional.

Referring to FIG. 4, three formulations are formed by adding the surfactant penetration enhancer, the compound containing 90% lauric acid diethanolamide and 6% diethanolamine, and polyethylene glycol glyceryl caprylate, to the formulation made with polyacrylic pressure sensitive adhesive Gelva 737 and 10% scopolamine. Gelva 737, for example, is provided by Monsanto company. The three formulations include: (1) polyacrylic pressure sensitive adhesive Gelva 737 and 10% scopolamine; (2) polyacrylic pressure sensitive adhesive Gelva 737, 10% scopolamine and 5% polyethylene glycol glyceryl caprylate; and (3) polyacrylic pressure sensitive adhesive Gelva 737, 10% scopolamine and 5% of the compound containing 90% lauric acid diethanolamide and 6% diethanolamine. The three curves show the results of a dermal penetrative test of the samples on the dermal horny layers substituted 2913. These include: (1) polyacrylic pressure sensitive adhesive Gelva 737 and 10% scopolamine 122; (2) polyacrylic pressure sensitive adhesive Gelva 737, 10% scopolamine and 5% polyethylene glycol glyceryl caprylate 124; and (3) polyacrylic pressure sensitive adhesive Gelva 737, 10% scopolamine and 5% of the compound containing 90% lauric acid diethanolamide and 6% diethanolamine 126. In accordance with the result showed in FIG. 4, the compound containing 90% coconut fatty acid diethanolamide and 6% diethanolamine enhances the dermal penetrative rate of scopolamine, but the enhanced effect of polyethylene glycol glyceryl caprylate is fractional. Polyethylene glycol glyceryl caprylate even decreases the dermal penetrative effect of scopolamine.

Figure 2:
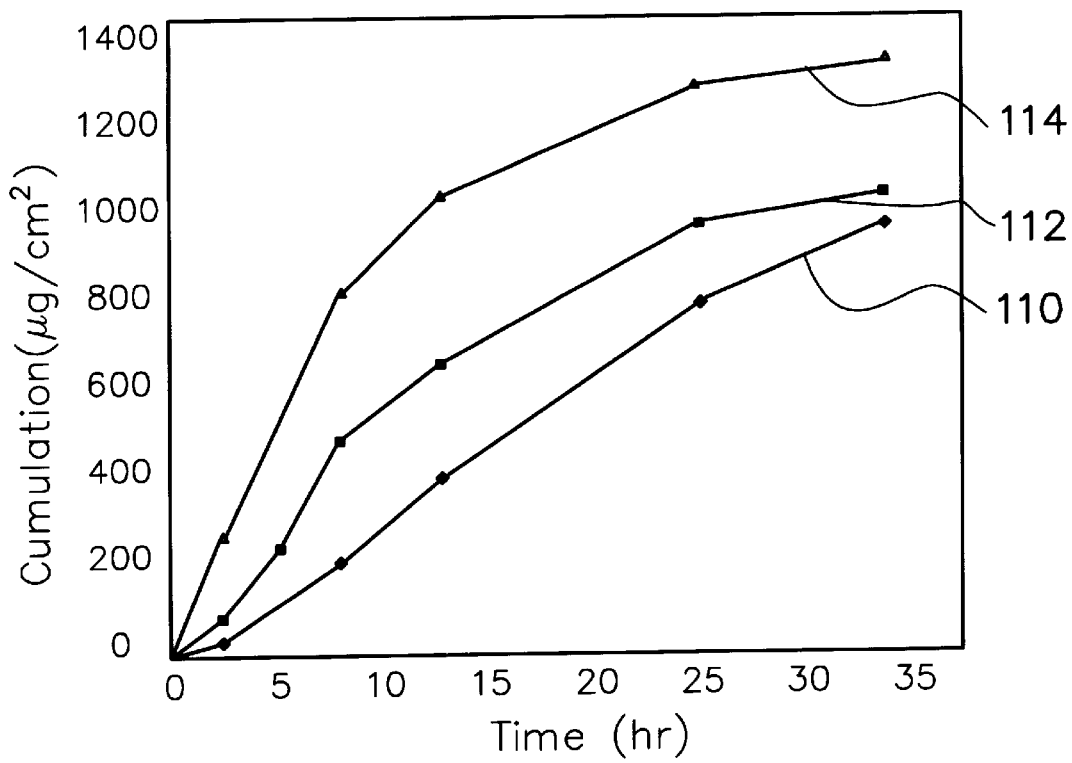
FIG. 2 is a diagram showing the effect of adding the dermal enhancer a compound containing 90% lauric acid diethanolamide and 6% diethanolamine, and polyethylene glycol glyceryl caprylate versus the polyacrylic pressure sensitive adhesive 2516 and 10% transdermal scopolamine added to the formulation of the present invention.
Figure 3:
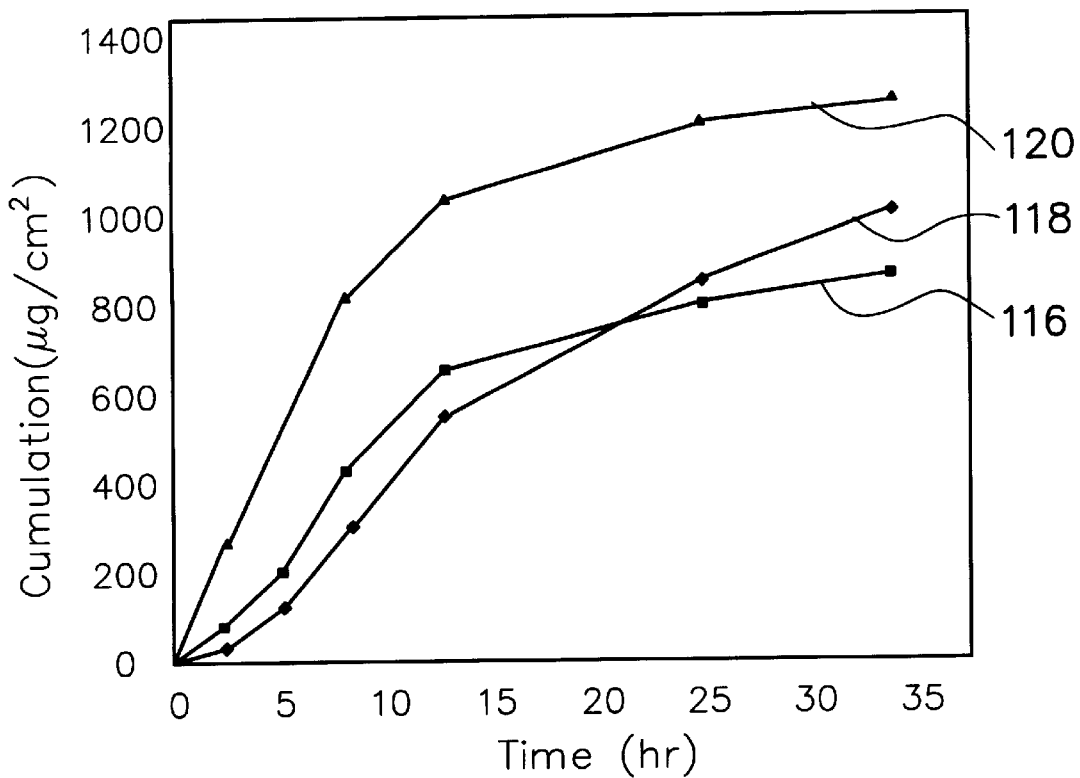
FIG. 3 is a diagram showing the effect of adding the dermal enhancer a compound containing 90% lauric acid diethanolamide and 6% diethanolamine, and polyethylene glycol glyceryl caprylate versus the polyacrylic pressure sensitive adhesive MA31 and 10% transdermal scopolamine added to the formulation of the present invention.
Figure 4:
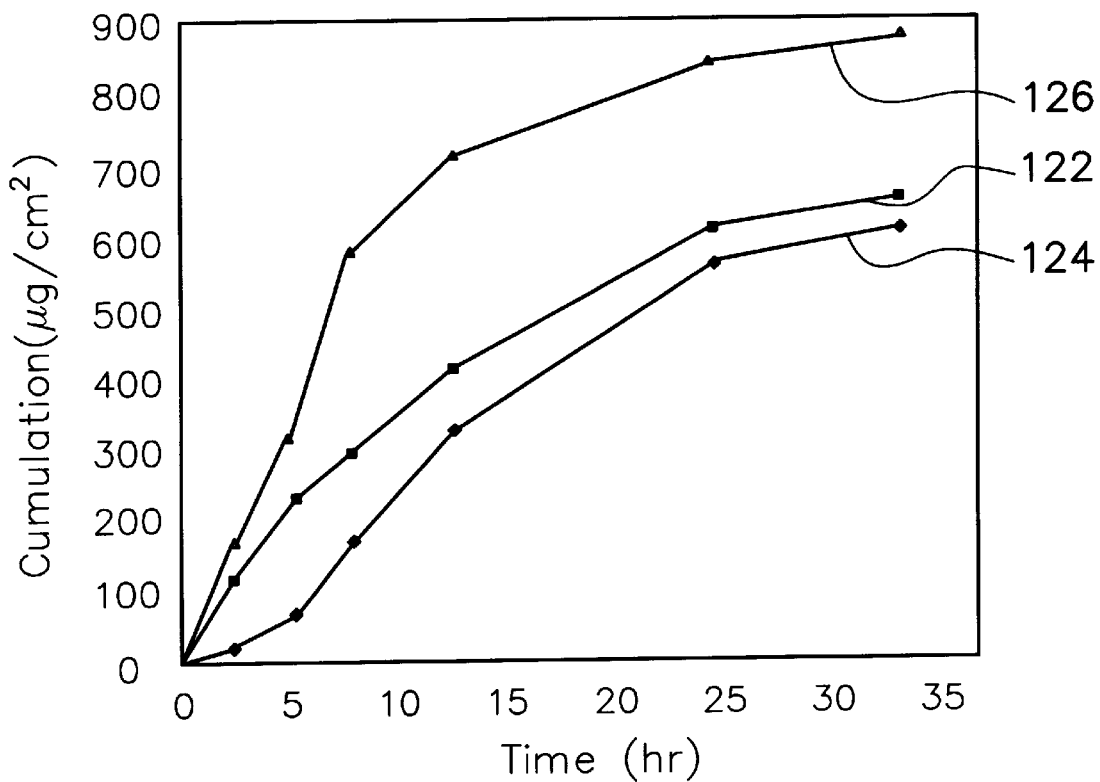
FIG. 4 is a diagram showing the effect of adding the dermal enhancer a compound containing 90% lauric acid diethanolamide and 6% diethanolamine, and polyethylene glycol glyceryl caprylate versus the polyacrylic pressure sensitive adhesive Gelva737 and 10% transdermal scopolamine added to the formulation of the present invention.

Through FIG. 2–FIG. 4, show the different dermal penetrative effects of the surfactant derivatives of amide and polyethylene in various polyacrylic pressure sensitive adhesives. On the whole, the enhanced effect of amide is better.

While the invention has been described by way of example and in terms of a preferred embodiment, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

What is claimed is:

1. A formulation for a cholinergic antagonist patch, comprising:

a polyacrylic pressure sensitive adhesive;

scopolamine; and a penetration enhancer selected from the group consisting of polyethylene glycol glyceryl caprylate and polyethvlene glycol-6 glyceryl mono oleate.

2. A formulation for a cholinergic antagonist patch according to claim 1, wherein the concentration of scopolamine is about 3%–20%.

3. A formulation for a cholinergic antagonist patch according to claim 1, wherein the concentration of the penetration enhancer is about 1%–5%.

4. A formulation for a cholinergic antagonist patch, comprising:

a polyacrylic pressure sensitive adhesive;

scopolamine; and a penetration enhancer comprising a compound containing 90% lauric acid diethanolamide and 6% diethanolamine.

5. A formulation for a cholinergic antagonist patch according to claim 4, wherein the concentration of the compound is about 2.5%.

6. A formulation for a cholinergic antagonist patch, comprising:

a polyacrylic pressure sensitive adhesive;

scopolamine; and a penetration enhancer comprising a compound containing 90% coconut fatty acid diethanolamide and 6% diethanolamine.

7. A formulation for a cholinergic antagonist patch according to claim 6, wherein the concentration of the compound is about 2.5%.

* * * * *